(12) United States Patent
Edelman et al.

(10) Patent No.: US 8,551,961 B2
(45) Date of Patent: Oct. 8, 2013

(54) LOCALIZED DELIVERY OF CARDIAC INOTROPIC AGENTS

(75) Inventors: Elazer Edelman, Brookline, MA (US); Mark Lovich, Brookline, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 966 days.

(21) Appl. No.: 11/440,529

(22) Filed: May 25, 2006

(65) Prior Publication Data
US 2007/0021358 A1 Jan. 25, 2007

Related U.S. Application Data

(60) Provisional application No. 60/684,594, filed on May 25, 2005.

(51) Int. Cl.
*A01N 45/00* (2006.01)

(52) U.S. Cl.
USPC .......................................................... 514/26

(58) Field of Classification Search
None
See application file for complete search history.

(56) References Cited

U.S. PATENT DOCUMENTS

| | | | |
|---|---|---|---|
| 3,987,200 A * | 10/1976 | Tuttle et al. ................... | 514/654 |
| 4,637,815 A | 1/1987 | Lemole | |
| 5,387,419 A * | 2/1995 | Levy et al. .................... | 424/422 |
| 5,900,433 A | 5/1999 | Igo et al. | |
| 6,726,920 B1 * | 4/2004 | Theeuwes et al. ............ | 424/422 |
| 2002/0055705 A1 | 5/2002 | Talpade | |
| 2002/0150622 A1 | 10/2002 | Philbrook et al. | |
| 2002/0188325 A1 | 12/2002 | Hill et al. | |
| 2003/0036773 A1 | 2/2003 | Whitehurst et al. | |
| 2003/0124503 A1 | 7/2003 | Olivencia-Yurvati et al. | |
| 2004/0034272 A1 | 2/2004 | Diaz et al. | |
| 2004/0039063 A1 | 2/2004 | Wink et al. | |
| 2004/0162346 A1 | 8/2004 | Lopaschuk et al. | |
| 2004/0199209 A1 | 10/2004 | Hill et al. | |
| 2005/0004428 A1 | 1/2005 | Cox et al. | |

FOREIGN PATENT DOCUMENTS

| | | |
|---|---|---|
| EP | 1 588 736 A2 | 10/2005 |
| WO | WO 99/36538 | 7/1999 |
| WO | WO 2005/118069 A1 | 12/2005 |

OTHER PUBLICATIONS

Stedman's Medical Dictionary—"inotropic."*
Wikipedia article—"Inotrope."*
Degenfeld et al. Cardiovascular Research 35 (1997) 233-240.*
Tinker et al. Anesthesiology, vol. 44, No. 4, Apr. 1976, pp. 281-286.*
Seguin et al. Clinical Pharmacology & Therapeutics, May 2002, pp. 381-388.*
Haider, et al., "Improved Cardiac Performance and Reduced Pulmonary Vascular Constriction by Epinephrine Administration Via a Left Atrial Catheter in Cardiac Surgical Patients" *Journal of Cardiothoracic and Vascular Anesthesia*, vol. 7 No. 6, 1993, pp. 684-687.
Fullerton, et al., "Hemodynamic Advantage of Left Atrial Epinephrine Administration After Cardiac Operations", pp. 1263-1266, 1993.
Skelding, et al., "Resolution of Refractory No-Reflow With Intracoronary Epinephrine", pp. 306-309, 2002.
Wilson S. Colucci, "Observations on the Intracoronary Administration of Milrinone and Dobutamine to Patients with Congestive Heart Failure", *The American Journal of Cardiology*, Jan. 1989, pp. 17A-22A.
"Invitation to Pay Additional Fees" for International Application No. PCT/US2006/020252 with an International Filing Date of May 25, 2006.
Hideaki Takai et al., "The Efficacy of Low Prime Volume Completely Closed Cardiopulmonary Bypass in Coronary Artery Revascularization". pp. 178-182, Ann Thorac Cardiovascular Suraery, vol. 10, No. 3., 2004.
Maria Helena L. Souza et al., "Weaning from Cardiopulmonary Bypass", Virtual Textbook of Extracorporeal Technology, 1999. Available at <http:perfline.com/textbook/local/weaning0399.html>.

* cited by examiner

*Primary Examiner* — Layla Bland
(74) *Attorney, Agent, or Firm* — Sutherland Asbill & Brennan LLP

(57) ABSTRACT

The present invention provides novel methods for the localized delivery of inotropic agents to the heart, including specific regions of the heart, such as the ventricles, for example in a subject undergoing cardiothoracic surgery, with the aim of supporting the myocardial contractile function of the heart.

16 Claims, 3 Drawing Sheets

LOCALIZED DELIVERY OF CARDIAC INOTROPIC AGENTS

CROSS REFERENCE TO RELATED APPLICATIONS

This application claims the benefit under 35 U.S.C. §119(e) of U.S. Provisional Patent Application Ser. No. 60/684,594 filed May 25, 2005, the contents of which are herein incorporated by reference in their entirety.

FIELD OF THE INVENTION

The present invention is directed to methods for the localized delivery of inotropic agents to the heart, including specific regions of the heart such as the ventricles, in a subject in need of such contractile support.

BACKGROUND OF THE INVENTION

Performance of cardiac surgery is a delicate and invasive procedure. The majority of epicardial bypass graft surgeries, and all open heart procedures, require temporary arrest of the heart to allow the surgeon to accomplish the required task without interference from heart movement. An extracorporeal machine, known as a cardiopulmonary bypass (CPB) circuit, assumes the heart and lungs' role of supplying oxygenated blood to the rest of the body while the heart is arrested. Once the surgery is completed, the heart must be re-started, and the patient weaned from the CPB.

While the use of CPB makes cardiac surgery feasible, it is also associated with significant risks and difficulties. The use of a CPB machine usually requires an aortic cross-clamp to separate the heart from the rest of the circulation. Because the coronary arteries arise very close to the heart, the cross clamp must be applied distal to their ostia and therefore they receive no blood flow for prolonged periods, and thus the heart becomes ischemic. Despite numerous myocardial protection strategies, such as hypothermia and chemical cardioplegia to decrease oxygen consumption by arresting the heart, many patients' heart function is significantly impaired by both chemical arrest and the CPB circuit itself. Chemical cardioplegia, altered coronary perfusion, embolic events and direct manual manipulation of the heart during the procedure all contribute to depression of myocardial function after it is restarted. Furthermore, the degree of post CPB dysfunction may depend on the duration of the CPB time. Patients emerge from chemical cardiac arrest with a spectrum of left ventricular dysfunction, from transient mild impairment to outright ventricular failure and inability to be separated from the CPB. Patients with preexisting ventricular dysfunction are at the greatest risk for further myocardial impairment during CPB.

Moreover, because of improvements in surgical technique and intraoperative myocardial protection, as well as the increasing availability of sophisticated valvular, direct myocardial resections, repairs of septal defects, and coronary bypass procedures, more cardiac operations are being performed on patients with more advanced stages of disease and decreased ventricular function. Indeed, the number of operative risk factors, including advanced age, female gender, severity of angina, triple vessel disease, and left ventricular dysfunction, has increased among patients currently undergoing coronary artery bypass surgery [Davis P K, et al., Ann Thorac Surg 1989; 47:493-98].

In addition, there are important, potentially damaging effects of CPB itself on the cardiovascular system, including increased capillary permeability with attendant transcapillary plasma loss, renal dysfunction, peripheral or central vasoconstriction, coagulopathy, platelet destruction and dysfunction, and destruction of red blood cells [Kalter R D, et al., J Thorac Cardiovasc Surg 1979; 77:428-35; Kirklin J K, et al., J. Thorac Cardiovasc Surg 1983; 86:845-57.]. Patients with preexisting cardiomyopathies are at even greater risk for postoperative contractile dysfunction. These effects are often transient, but their timing and intensity can make it difficult to impossible in many instances to separate the patient from the CPB circuit.

Weaning a patient off cardiopulmonary bypass (CPB) is a critical step of cardiac surgical procedures. Restarting the heart and returning it and the lungs to the circulation after CPB carries the potential to severely stress an already compromised heart. In the best of circumstances, weaning off CPB can be a relatively straightforward process that requires reestablishing ventilation to the lungs and slowly lowering the circulatory support from the CPB pump. In a significant number of cases however, weaning is especially difficult, and in a few situations simply impossible.

Current available options to support patients who fail to wean from CPB, in order of increasing invasiveness and associated morbidity, include intravenous infusion of inotropes that enhance myocardial contractility, insertion of an intra-aortic balloon pump to augment coronary perfusion and diminish the workload on the heart, and placement of a ventricular assist device. However, each of these treatments is accompanied by significant morbidity and technical limitations, and potential toxicity. Examples of limitations associated with such treatments include proarrhythmic and systemic effects from systemic infusion of inotropes, damage from large-bore indwelling vascular access, need for patient immobility and sedation, as well as risks associated with the placement of a large mass of foreign materials with externalized connections. The pumps and devices have high rates of infection and thromboembolic complications, and require patient immobility, sedation, sometimes prolonged postoperative ventilation, and the most extreme of intensive care nursing support. Weaning of small children after prolonged, difficult and complex operations can represent a further challenge to the surgical team as assist devices may not be readily available in appropriate sizes.

One of the significant challenges of supporting patients as they transition from CPB to the intensive care unit is the variability between patients regarding the timing and degree of support each patient requires. Many patients only need short-term inotropic support to help them transition from CPB to the intensive care unit, while the support required by other patients is much more extensive and potentially associated with greater risks. Thus, it would be desirable to have less intrusive means that could be used to support these patients as they transition off CPB.

Inotropic agents are one approach used to enhance a high-risk patient's ability to wean from CPB. Pharmacologic inotropic agents enhance myocardial contractility, and fall into two broad categories: sympathomimetics such as epinephrine (adrenaline), norepinephrine (noradrenaline), dobutamine, isopreterenol, salbutamol, salmeterol, terbutaline, isoproterenol, phenylephrine, ephedrine, clonidine and dopamine, and phosphodiesterase inhibitors such as milrinone and amrinone. Each of these compounds, while increasing the inotropic state of the heart, has limitations that restrict the doses that can be given intravenously and often necessitate infusion of additional agents to counteract side effects. For example, dopamine dosing is limited by the increase in the rate and irritability of electrical excitation of the heart that accompanies the desired inotropic effect. Alternatively, phosphodiesterase inhibitors increase intracellular cyclic AMP, an intracellular signaling molecule that increases inotropy, but unfortunately dilates arterioles and causes systemic vasodilation and hypotension. As a result, vasoconstricting sympathomimetic agents often need to be co-administered and these again can lead to proarrythmogenic states and undesirable tachycardia.

One important consideration of the use of inotropic agents is that they are administered systemically and thus treat all vascular beds. Systemic side effects of sympathomimetics include potential renal and cerebral vasoconstriction, and pulmonary artery hypertension, which in turn can induce right heart failure. Other undesired effects are excess tachycardia and electrical irritability.

Accordingly, there is a need for improved methods to support patients as they transition off CPB, by improving contractile function of the heart without extraventricular effects, such as tachycardia, vasoconstriction or systemic hypotension.

SUMMARY OF THE INVENTION

The present invention provides novel methods for the localized delivery of inotropic agents to the heart, including specific regions of the heart, such as the ventricles, in a subject in need thereof.

Support of the weakened heart such as occurs while a patient is coupled to a CPB circuit, and while the patient transitions off CPB, is critical to recovery from cardiac surgery. We have discovered methods to take advantage of existing polymeric controlled release strategies to deliver inotropic agents directly or indirectly to the heart, preferably directly, including to specific regions of the heart. By locally delivering the inotropic agent directly to the heart, the systemic exposure of the inotropic agents is limited, avoiding the alterations in vascular tone, and heart rate and electrical excitability associated with systemic administration of these agents.

The methods of the present invention can be used to treat any patient in need of transient contractile support to the heart, where such support can be provided by the local delivery of inotropic agents either directly or indirectly to the heart, including specific regions of the heart, such as the ventricles. One would apply the agent through the cardiac blood stream, or preferably directly in the heart. The agent can be applied through the coronary artery or vein and onto the heart surface. The agent can also be applied through the ventricular or atrial walls and onto the heart surface. The agent can also be applied through direct and extensive surgical field exposure, minimally invasive exposure via a pericardial window or heart port, or percutaneous or endovascular catheters.

In one embodiment, the patient is in need of localized delivery of an inotropic agent to provide contractile support as a result of a surgical intervention. Surgical interventions include but are not limited to cardiac surgery, thoracic surgery, and general surgery. In another embodiment, the patient is in need of transient localized delivery of an inotropic agent to provide contractile support as a result of trauma, shock, or heart failure.

In another embodiment, the patient is in need of transient inotropic support following an intervention less invasive than a major surgical intervention, referred to herein as a minimally invasive intervention. Such minimally invasive interventions include but are not limited to a percutaneous intervention or a catheter based intervention. In such embodiments, the inotropic agent can be delivered either from inside the heart chamber or from outside the heart.

One preferred embodiment provides transient localized delivery of inotropic agents to support the heart of a patient undergoing surgery. In one embodiment, the patient requires support from a cardiopulmonary bypass (CPB) circuit. In another embodiment, the patient does not require support from a CPB circuit. In one particularly preferred embodiment, the patient is a cardiac patient.

The present invention provides the local delivery of any inotropic agent, including but not limited to sympathomimetics and phosphodiesterase inhibitors. Preferred sympathomimetics include epinephrine, norepinephrine, isoproterenol, dobutamine and dopamine, and analogues and derivatives thereof. Preferred phosphodiesterase inhibitors include milrinone and amrinone, and analogues and derivatives thereof.

Any delivery vehicle which can be loaded with an inotropic agent and directly applied to the heart can be used in the present invention. Delivery vehicles include drug-impregnated, coated or releasing sheets, patches, matrix, hydrogel, foam, gel, cream, spray, microsphere, microcapsule, composite and ointment. Certain preferred delivery vehicles are polymeric controlled release vehicles.

The delivery vehicle is loaded with the inotropic agent and locally applied to the heart using any route for application which allows its local application to the heart. In one embodiment, the delivery vehicle may be applied directly to the exposed heart during a surgical intervention, for example before the pericardium or sternum is closed. In another embodiment, the delivery vehicle may be applied through a less direct route, including but not limited to a percutaneous application or an endovascular injection.

Certain embodiments of the invention provide further localization of the delivery of the inotropic agent. In one embodiment, the delivery vehicle is placed away from the sinoatrial node or the right atrium. A preferred placement of the delivery vehicle is on the left ventricular free wall or apex of the ventricle.

One particularly preferred embodiment provides local delivery of dopamine to the ventricle without targeting the sinus node in the right atrium, limiting the excessive tachycardia observed in high dose intravenous infusion of this agent.

Another embodiment of the invention provides the use of a non-permeable barrier on the surfaces of the heart not treated with the delivery vehicle, to achieve additional localization. In another embodiment of the invention, non-permeable barriers can be used to direct drug toward the myocardium and prevent the loss of drug to ventricular blood flow or pericardial fluid.

Preferably, the delivery methods of the present invention are administered to the subject for a short time, i.e. just long enough to support the heart until it recovers from its weakened condition. Administration of the inotropic agent may last for a few hours to days, for example up to 14 days. The delivery methods of the present invention can be used to treat the heart prior to surgery, during surgery, after surgery, and any combination thereof.

DETAILED DESCRIPTION OF THE INVENTION

Figure 1:
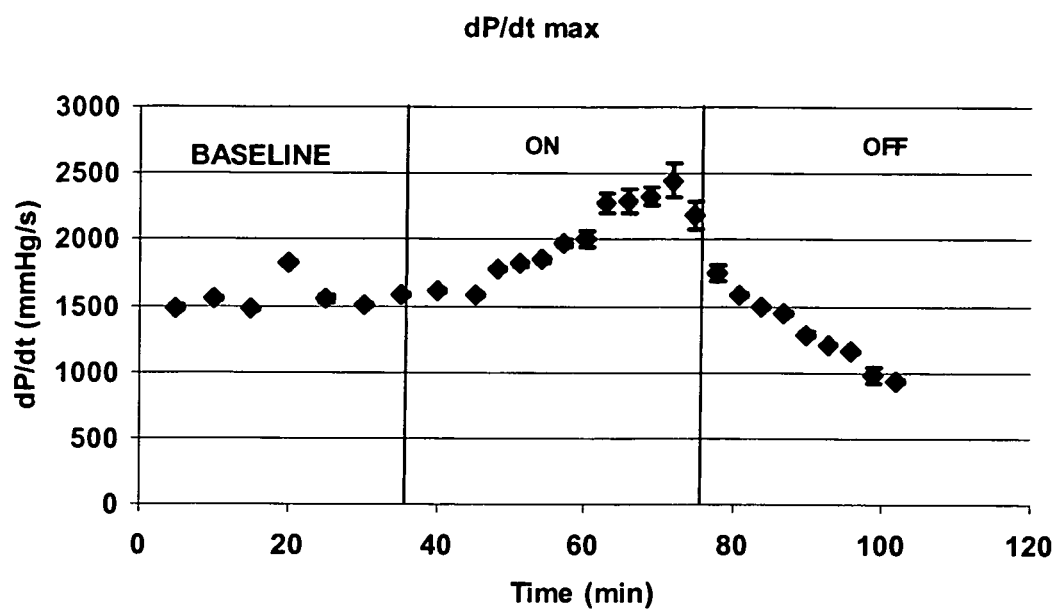
FIG. 1 shows contractility of the heart (max dp/dt (mmHg/s)) over time in rats administered dobutamine, a non selective beta agonist inotropic agent, which was delivered directly to the left ventricular wall. Contractility was significantly increased shortly after dobutamine was applied to the surface of the heart.

The present invention provides novel methods for the localized delivery of inotropic agents to the heart, including specific regions of the heart, in a subject in need of transient contractile support. One embodiment provides localized delivery of inotropic agents to support the heart during or following cardiac surgery, including as a subject transitions off of a cardiopulmonary bypass (CPB) circuit.

The present invention provides advantages over known methods to support the weakened heart, such as while a cardiac surgery patient is coupled to a CPB circuit, and as a patient transitions off CPB. To avoid the adverse side effects associated with systemic delivery of positive inotropic agents, we have discovered methods to take advantage of existing polymeric controlled release strategies to locally deliver inotropic agents directly to the heart. By locally delivering the inotropic agent directly to the heart, the systemic exposure of the inotropic agents is limited, avoiding the peripheral arterial dilation and systemic hypotension associated with systemic administration of some of these agents, and the tachycardia and vasoconstriction associated with others. In addition, because the methods of the invention deliver the positive inotropic agent directly to localized heart surface, lower amounts, but potentially high local concentrations, can be delivered.

The inventors of the present invention have surprisingly shown that inotropic agents, when applied directly to the heart rather than systemically, increase contractility of the heart and minimize systemic side effects such as the reduction in systemic blood pressure that is seen when certain inotropic agents, such as dobutamine, isoproterenol, milrinone, or amrinone are administered systemically. Thus, the inventors have shown that local delivery of inotropic agents minimizes systemic side effects while improving contractile function of the heart.

In one embodiment, a method of locally delivering a cardiac inotropic agent to the heart of a subject is encompassed. This method comprises locally administering to a subject in need thereof a therapeutically effective amount of at least one inotropic agent.

In one embodiment, the inotropic compound is an agent that interacts with the sympathetic nervous system and modulates calcium entry, G-proteins, ATP, or GTP, wherein the inotropic agent is selected from the group consisting of sympathomimetic compounds, phosphodiesterase inhibitors, BNP, ANP, and digitalis glycosides, and derivatives and analogues thereof.

The inotropic agent may be a sympathomimetic compound selected from the group consisting of epinephrine, norepinephrine, dobutamine, isoproterenol, salbutamol, salmeterol, terbutaline, phenylephrine, ephedrine, clonidine and dopamine, and derivatives and analogues thereof.

Alternatively, the inotropic agent may be a phosphodiesterase inhibitor selected from the group consisting of milrinone and amrinone, and derivatives and analogues thereof.

The subject to be treated may be a surgical patient. Non-limiting examples of surgical patients are a cardiac surgery patient, a thoracic surgery patient, and a general surgery patient.

In one embodiment, the cardiac surgery patient is selected from the group consisting of a cardiac surgery patient requiring support from a cardiopulmonary bypass circuit and a cardiac patient not requiring support from a cardiopulmonary bypass circuit.

In another embodiment, the subject has a condition selected from the group consisting of trauma, shock, and acute and chronic congestive heart failure.

In one embodiment, the inotropic agent is locally delivered to the heart by administering the inotropic agent directly to the heart via an open surgical wound. Alternatively, the local delivery comprises administering said inotropic agent directly to the heart percutaneously.

A method of reducing postoperative complications of cardiopulmonary bypass (CPB) surgery in a subject is also encompassed in the present invention. This method comprises locally administering to a subject in need thereof an effective amount of an inotropic agent in conjunction with CPB surgery of said subject. The inotropic agent may be a sympathomimetic compound or a phosphodiesterase inhibitor.

The inotropic agent may be administered to said subject during a time period consisting of 1) prior to said CPB surgery; 2) during said CPB surgery; 3) subsequent to said CPB surgery; and 4) combinations thereof.

As used herein, a "therapeutically effective amount" of the inotropic agent is an amount that is sufficient to effect myocardial contractility.

The inotropic agent may be delivered locally to the heart by its inclusion in a delivery vehicle.

Subjects for Administration

The methods of the present invention can be used to treat any patient in need of transient contractile support to the heart, where such support can be provided by the local delivery of inotropic agents directly to the heart, including specific regions of the heart, such as the ventricles.

In one embodiment, the patient is in need of localized delivery of an inotropic agent to provide transient contractile support as a result of a surgical intervention. Surgical interventions include major surgeries, including but not limited to cardiac surgery, thoracic surgery, and general surgery. In another embodiment, the patient is in need of localized delivery of an inotropic agent to provide contractile support as a result of trauma, shock, or heart failure.

In another embodiment, the patient is in need of inotropic support following an intervention less invasive than a major surgical intervention, referred to herein as a minimally invasive intervention. Such minimally invasive interventions include but are not limited to a percutaneous intervention or a catheter based intervention. In such embodiments, the introtropic agent can be delivered either from inside the heart chamber or from outside the heart, as described in detail below.

One preferred embodiment provides localized delivery of inotropic agents to support a patient undergoing surgery. In one embodiment, the surgical procedure requires the use of a cardiopulmonary bypass (CPB) circuit. In another embodiment, the procedure does not require the use of a CPB circuit. In one particularly preferred embodiment, the patient is a cardiac patient.

In order to perform many surgical procedures it is necessary to interrupt coronary blood flow. Without cardioprotective strategies such as cooling and chemical arrest, the heart would soon die. Unfortunately, no cardioprotective strategy has been shown to be optimal and some degree of post CPB contractile dysfunction is inevitable. This is not only a problem in the adult patient undergoing coronary artery bypass surgery (CABG) or other surgical procedures, it is also a significant clinical problem during surgical heart procedures to correct congenital heart defects in neonates.

Thus, local administration of the agent can begin at any time once surgery begins until twenty-four hours after surgery has ended. More typically, within 12 hours of surgery ending. Any range within these ranges can be used, such as 1, 2, 3, 4, or more hours after surgery has ended.

In certain embodiments, administration of the agent can begin before surgery, for example using a percutaneous approach for delivery of the agent.

Accordingly, the methods of the present invention can be used to treat any subject while coupled to a CPB circuit, i.e. during cardiac surgery, and/or following cardiac surgery, during their transition off of the CPB circuit. Cardiac surgery includes any surgical procedure on the heart and usually involves interruption of coronary blood flow. It can also be used to assist the heart function during and after any thoracic surgical procedure where the heart is already exposed to the surgeon.

Before turning the CPB circuit, also known as the pump, off, all clinical determinants of cardiac performance are evaluated and adjusted, in order to optimize cardiac output. All metabolic, thermal, electrolyte, acid/base, and hematologic abnormalities are corrected. Blood volume is adjusted according to central venous, left atrial or pulmonary artery pressures. Peripheral resistance is estimated and vasodilators or constrictors are instituted as required. After the drug's effectiveness is assessed, pump flow is decreased in small increments while venous return to the heart is proportionately adjusted to maintain a constant filling pressure by constricting the venous drainage to the CPB circuit.

The assessment of cardiac function by transesophageal echocardiography and hemodynamic data immediately before terminating CPB allows patients to be classified into 3 groups by decreasing risk, referred to herein as groups A, B, and C [Souza et al., Indian Journal of Extracorporeal Technology 6:2, 1998]. The methods of the present invention can be used to treat any patient in group A, B, or C, including children in need of inotropic support during cardiac surgery or during weaning from CPB.

The highest risk patients, classified herein as "Group A" patients, have severe cardiac dysfunction that makes it difficult to be removed from CPB, despite physiologic and pharmacological support. For these patients CPB is prolonged. Group A patients are by definition the hardest cases to manage. A few of these patients by the end of rewarming of the blood will have minimal or no cardiac activity, which precludes any trial of disconnection from pump. The remaining patients may be given a short trial off pump after optimization of preload, afterload and contractility by a combination of inotropes and vasoactive agents. Some of these patients will tolerate CPB removal, under maximal physiological and pharmacological support, and a few in the group may be further improved by an intra-aortic balloon pump. The patients with minimal cardiac activity and those in whom the trial off pump was unsuccessful are temporarily maintained on cardiac support with the heart-lung machine. A few hours on pump support may be a sufficient rest period to allow recovery of cardiac function and removal of CPB support in a small number of cases. For the others, a decision has to be made as to either advance to a mechanical device for prolonged support or terminate the efforts to recover cardiac action.

Children in Group A supported by full veno-arterial extracorporeal membrane oxygenation (ECMO) post cardiotomy have a poor long term survival rate [Langley et al., Eur J Cardiothorac Surg 13, 520-5, 1998] when compared with children managed with centrifugal ventricular assist devices [Thuys et al., Eur J Cardiothorac Surg 13, 130-4, 1998]. The methods of the present invention may be utilized in the treatment of children in Group A.

In certain cases, a few hours of circulatory assistance and intensive inotropic and vasodilator drug therapy may turn some Group A patients into group B. The remaining patients are candidates to a form of total circulatory mechanical support (if available) or they will not likely survive disconnection from pump [Harris C. et al., Tecnol. Extracorp. Rev. Latinoamer. 3, 13-19, 1996; El-Banayosy A., et al., Perfusion, 11, 93-102, 1996; Núñez H I., Tecnol. Extracorp. Rev. Latinoamer. 2, 3341, 1995].

Group B patients have a mild to moderate degree of cardiac dysfunction, and require greater support and a more elaborate protocol for CPB termination than patients in Group C. Final preparations are made on partial bypass. In addition to the delivery of inotropic agents using the present invention, these patients may also be supported by physiological means such as volume resuscitation or additional pharmacological means, namely vasodilators. Some patients in this group can benefit from intra-aortic balloon pumping. Patients in this group will benefit from the methods of the present invention.

Some Group B patients may have to return to pump for better adjustment of drugs, or to have an intra-aortic balloon inserted if a marginal cardiac output is present, as demonstrated by atrial and arterial pressures, arterial and venous blood gases and pH, and spontaneous diuresis.

Group B patients include children with preoperative intracardiac shunts leading to high pulmonary blood flow, children after a heart transplant, and some adults with long standing congestive heart failure, who may present with pulmonary hypertension that precludes successful weaning. In certain instances, inhalation of nitric oxide (NO) can improve pulmonary hypertension and cardiac output and support discontinuance of CPB. Additional Group B patients include patients who received inadequate myocardial protection for any reason, including inadequate re-dosing of cardioplegia, inadequate perfusion of myocardia with cardioplegia, patients with severe ventricular hypertrophy or aortic insufficiency, surgical errors, and prolonged CPB time.

An occasional patient in group B will not tolerate CPB termination even after a few trials. These few exceptions turn into group A patients.

For lower risk "Group C" patients, inotropic support of the present invention can be provided at a lower level, and may be discontinued as the patient arrives at the intensive care area or a few hours thereafter. The methods of the present invention can be used as needed to treat Group C patients, who are anticipated to smoothly disconnect from perfusion. For these patients, after reestablishing ventilation to the lungs, pump flow can be gradually reduced while venous return to the oxygenator is decreased until bypass is minimal. Arterial pump is stopped and venous line is clamped. Final adjustment of cardiac performance is made off pump, by slowly administering residual volume from the oxygenator until ideal preload is attained. These patients maintain an adequate cardiac output, as can be confirmed by normal atrial and arterial pressures, arterial and venous blood gases and pH and adequate spontaneous diuresis.

In one particularly preferred embodiment of the invention, the methods can be used to treat any subject undergoing non cardiac thoracic surgery where the heart is exposed, to assist the heart function and/or to treat contractile dysfunction.

In some embodiments, the inotropic agent of the present invention can be co-administered with prostaglandin E1, which can act as a powerful adjunct to wean difficult transplanted children with right ventricular failure.

In some embodiments, the inotropic agent of the present invention can be co-administered with nitroprusside or other vasodilator drugs.

In some embodiments, one particularly preferred inotrope is enoximone, to provide pharmacological support during weaning of patients with severe ventricular dysfunction.

The term "subject" as used herein refers to vertebrates, particularly members of the mammalian species and includes but is not limited to, domestic animals, sports animals, primates, dogs, cats, rodents including mouse and rat, horse and humans; more preferably, the term refers to humans.

Inotropic Agents

As used herein, "inotropic agents" or "positive inotropic agents" or "inotropes" or "positive inotropes" or "inotropic antibodies" will be used interchangeably and refers to the effect such agents produce, i.e. improves cardiac output by increasing the force of myocardial muscle contraction. "Positive inotropic effect" means that the contractility of the cells is enhanced in a dose-dependent manner. A positive inotropic effect-producing amount of an inotropic agent of the invention can be administered to a subject.

Positive inotropic agents of the present invention include any agents which provide the heart with contractile support. The agent can be an inotropic agent such as a sympathomimetic or a phosphodiesterase inhibitor, as long as one obtains the desired contractile effect on the heart. Inotropic compounds include agents that interact with the sympathetic nervous system and modulate calcium entry, G-proteins, ATP and GTP. Inotropic compounds include sympathomimetic compounds, phosphodiesterase inhibitors, BNP, ANP, and digitalis glycosides. Preferably, the agent is a sympathomimetic or a phosphodiesterase inhibitor. Preferred sympathomimetics include but are not limited to epinephrine, norepinephrine, dopamine, dobutamine, dopexamine, terbutaline, and isoproterenol, and analogues and derivatives thereof. Preferred phosphdiesterase inhibitors include but are not limited to milrinone, amrinone, enoximone, and pimobendan, and analogues and derivatives thereof.

Preferably, the positive inotropic agent is administered in the form of a pharmaceutical composition. A pharmaceutical composition comprising an effective amount of the positive inotropic agent as an active ingredient can be prepared by standard procedures well known in the art, with pharmaceutically acceptable non-toxic solvents and/or sterile carriers, if necessary. For example, the inotropic agent can be embedded in a controlled-release polymer. In other embodiments the positive inotropic agent is administered without a pharmaceutical carrier.

The dose of the positive inotropic agent is a therapeutically effective dose. In particular embodiments, the positive inotropic agent can be administered at a dose which produces in the subject an effect equivalent to the systemic intravenous administration of between 2 and 20 mcg/kg/min. However, in other embodiments, higher and lower dosages can be administered to subjects. For example, a dose which produces in the subject an effect equivalent to the systemic intravenous administration of 0.5 mcg/kg/min, or 40 mcg/kg/min. Optimizing therapy to be effective across a broad population can be performed with a careful understanding of various factors to determine the appropriate therapeutic dose. Typically, the dose can be much lower than the dose administered by intravenous infusion, because the agent is being locally delivered to the heart, rather than systemic administration.

Localization of the Delivery Vehicle on the Heart

Routes for direct application of the delivery vehicle to the heart include any routes which allow the delivery vehicle to be applied locally to the heart. For example, the delivery vehicle may be applied from the blood stream, by being placed directly in the heart through the coronary arteries or veins onto the heart surface; or through the ventricular or atrial walls and onto the heart surface. The delivery vehicle may also be applied through direct application during extensive surgical field exposure, or through direct application during minimally invasive exposure, for example through a pericardial window or heart port. The delivery vehicle may also be applied through a percutaneous route, or via endovascular catheters.

In one embodiment, the delivery vehicle is loaded with the inotropic agent and placed over the heart of a surgical patient, before the sternum is closed, allowing direct release of the inotropic agent to the heart.

Placement of the delivery vehicle can be understood with reference to the different compartments of the heart. The heart is subdivided by a muscular septum into two lateral halves, which are named respectively right and left. A transverse constriction subdivides each half of the heart into two cavities, or chambers. The upper chambers consist of the left and right atria, which collect blood and help fill the lower chambers. The lower chambers consist of the left and right ventricles, which pump blood to the rest of the body. The chambers are defined by the epicardial wall of the heart. The right atrium communicates with the right ventricle by the tricuspid valve. The left atrium communicates with the left ventricle by the mitral valve. The right ventricle empties into the pulmonary artery by way of the pulmonary valve. The left ventricle empties into the aorta by way of the aortic valve.

The circulation of the heart consists of two components. First is the functional circulation of the heart, i.e., the blood flow through the heart from which blood is pumped to the lungs and the body in general. Second is the coronary circulation, i.e., the blood supply to the structures and muscles of the heart itself. The functional circulation of the heart pumps blood to the body in general, i.e., the systemic circulation, and to the lungs for oxygenation, i.e., the pulmonic and pulmonary circulation. The left side of the heart supplies the systemic circulation. The right side of the heart supplies the lungs with blood for oxygenation. Deoxygenated blood from the systematic circulation is returned to the heart and is supplied to the right atrium by the superior and inferior venae cavae. The heart pumps the deoxygenated blood into the lungs for oxygenation by way of the main pulmonary artery. The main pulmonary artery separates into the right and left pulmonary arteries, which circulate to the right and left lungs, respectively. Oxygenated blood returns to the heart at the left atrium via four pulmonary veins. The blood then flows to the left ventricle where it is pumped into the aorta, which supplies the body with oxygenated blood.

The functional circulation supplies blood to the heart by the coronary circulation. The coronary arteries arise from the proximal aorta through the left and right coronary ostia course along the epicardial surface of the heart and send of numerous branches to supply the myocardium. Blood is cleared from the muscle by cardiac veins that flow into the coronary sinus and right atria. The heart wall is surrounded by a pericardial sac, which contains it within interstitial fluid.

In one embodiment, the delivery vehicle loaded with the inotropic agent is placed over the heart, before the sternum is closed, allowing direct release of the inotropic agent to the heart. In one embodiment, the delivery vehicle is placed away from the sinoatrial node or the right atrium. A preferred placement of the delivery vehicle is on the apex of the ventricle or left ventricular free wall.

Another embodiment of the invention provides the use of a non-permeable barrier on the surfaces of the heart not treated with the delivery vehicle, to achieve additional localization. In another embodiment, the delivery vehicle itself can be coated with a non-permeable barrier, to further localize release of the agent directly to the underlying heart tissue, while minimizing release into the pericardial fluid.

One particularly preferred embodiment provides local delivery of dopamine, epinephrine, norepinephrine, isoproterenol, and dobutamine to the ventricle without targeting the sinus node in the right atrium, limiting the excessive tachycardia observed in intravenous infusion.

In one embodiment, the delivery vehicle contains an inotropic agent that must be activated or released by a second agent. That second agent can be added systemically to locally activate or release the inotropic agent. In this way, timing and/or release can be controlled at later points.

Treatment Period

Preferably, the delivery methods of the present invention are administered to the subject just long enough to support the heart until it recovers from its weakened condition. The short term or transient administration of the inotropic agent may last for a period of several minutes to several days. For example, from five minutes to 14 days. Typically, at least two hours to seven days. Preferably five hours to five days. More preferably, 2-24 hours. One can use all ranges between 5 minutes to 14 days, e.g. 12 hours to 12, 11, 10, 9, 8, 7, or fewer days.

In one embodiment of the invention, the patient is a surgical patient and the delivery methods of the present invention can be used to treat the heart prior to surgery, during surgery, after surgery, and any combination thereof.

Delivery Vehicle

The delivery vehicle of the present invention is any drug delivery means that can incorporate an inotropic agent, and is suitable for administration directly to the heart for local delivery or release of that agent. Suitability for local delivery to the heart includes the ability of a delivery vehicle to adhere to the underlying tissue. Any delivery vehicle which can be loaded with an inotropic agent and locally applied to the heart can be used in the present invention.

Examples of delivery vehicles include but are not limited to a patch, a matrix, a hydrogel, a sheet of material, a foam, a gel, a cream, a spray, and an ointment. Certain preferred delivery vehicles are polymeric controlled release vehicles. In one embodiment, the delivery vehicle is a patch, such as a transepicardial patch, that slowly releases the agents directly into the myocardium. In one embodiment, the delivery vehicle is an ointment or cream which may be placed manually on the target area of the heart. In one preferred embodiment, the delivery vehicle is a hydrogel, which may be polymerized either directly on the heart in vivo or polymerized in vitro to form a patch for administration.

In one preferred embodiment, the inotropic agent(s) of the invention are incorporated into a biocompatible delivery vehicle referred to as a matrix. The matrix can be in the form of a gel, foam, suspension, microcapsules, solid polymeric support, or fibrous structure. The matrix may also serve in a physically supporting role. There is no specific requirement as to thickness, size or shape. It is preferred that the matrix be sufficiently porous to allow the inotropic agent to diffuse out of the matrix into the surrounding tissue in roughly physiologic quantities.

Preferably, the matrix is a biodegradable material. Preferably, the hydrogel matrix degrades in a period of time minimizing tissue inflammation, for example in less than seven to ten days. Examples of a biodegradable matrices include but are not limited to synthetic polymers degrading by hydrolysis, for example, polyhydroxy acids like polylactic acid, polyglycolic acid and copolymers thereof, polyorthoesters, polyanhydrides, proteins such as gelatin and collagen, or carbohydrates or polysaccharides such as cellulose and derivatized celluloses, chitosan, alginate, or combinations thereof, so that over the course of several days or weeks after implantation of the matrix material, the matrix gradually disappears.

The use of biodegradable matrices eliminates the need for surgery to remove undegraded implanted matrix. However, synthetic non-biodegradable matrices may also be used. Useful materials include but are not limited to ethylene vinyl acetate, polyvinyl alcohol, silicone, polyurethane, non-biodegradable polyesters, and polyethyleneoxide-polypropyleneoxide, and tetrafluoroethylene meshes (Teflon®).

In a preferred embodiment, the matrix is a hydrogel, defined as a matrix wherein typically approximately 900-fold by weight of the matrix is absorbed water. Hydrogels are well known in the art. Hydrogels can be formed by ionic or covalent crosslinking of a variety of water soluble polymers such as polyphosphazenes, polysaccharides such as alginate, and proteins such as gelatin. For example, one matrix material is purified gelatin-based Gelfoam™ (The Upjohn Co., Kalamazoo, Mich.) surgical sponge.

To achieve the above properties, the hydrogel is formed primarily of polymerized macromers, the macromers being themselves polymers or copolymers of one or more monomers having reactive groups providing resorbable linkages and polymerizable sites for biodegradability and polymerization. The macromers have sufficient hydrophilic character to form water-absorbent polymerized gel structures, and are at least dispersible in a substantially aqueous solution, and preferably are water-soluble, to maximize tissue adherence. The macromers are preferably made predominantly of synthetic materials. The resulting hydrogels are preferably highly compliant, so as not to impede the process of cardiac contraction. The hydrogels are preferably covalently crosslinked to ensure that they are retained at the site of application until the hydrogels degrade. In certain embodiments, the gel can be crosslinked in situ, for example by photopolymerization.

Monomers and macromers which are suitable for forming the hydrogels ("referred to here in this section collectively as "monomers") have one or more of the following properties: water soluble, partially macromeric character, containing hydrophilic groups, and being covalently reactive. When crosslinked to form gels, the resulting gels are tissue adhesive, elastic, and compliant. The monomers are preferably water soluble. Water soluble materials are soluble to at least about 0.1 gram per liter of a substantially aqueous solvent. A substantially aqueous solvent comprises at least about 50% by weight of water, and less than about 50% by weight of a non-aqueous, water-miscible solvent. If the polymers are not entirely water-soluble, they should be dispersible in water, and form micelles, typically with the aid of non-aqueous, water-miscible solvents. The non-aqueous solvent must be present in an amount that does not damage the tissue. Thus only a small amount of non-aqueous, water-miscible solvent should be present in the pre-gelled composition to minimize tissue irritation. Up to about 10% by weight of the solution can be a non-aqueous, water-miscible solvent. Examples of non-aqueous, water-miscible solvents include ethanol, isopropanol, N-methylpyrrolidone, propylene glycol, glycerol, low molecular weight polyethylene glycol, DMSO, Benzyl alcohol, and benzyl benzoate. Liquid surfactants, such as poloxamers (e.g., PLURONIC™ surfactants) and some polyethylene glycol derivatives (e.g., some TWEEN™ surfactants) can also be used as non-aqueous, water-miscible solvents.

The monomers are preferably at least partially macromeric, and are more preferably substantially to completely macromeric. Macromers tend to be innocuous to tissue because they will not readily diffuse into or penetrate cells. A macromer is a reactive monomer consisting of a polymeric material with a number-average or weight-average molecular weight of about 500 Daltons or more and at least one reactive group. To form a crosslinked gel by chain-growth polymerization, the macromers, along with any other smaller monomers, in a solution must contain on average more than one reactive group (which may be a covalently reactive group, or a group that binds non-covalently to other macromers). For polymerizations involving step-growth polymerization, the macromers must contain on average more than two reactive groups, and the solution typically contain approximately equal numbers of the two different types of reactive groups. An example of step-growth polymerization is gelation by formation of urethane linkages from the reaction of isocyanate with the hydroxyl groups. For free-radical polymerization of unsaturated materials (chain-growth polymerization), the monomers must contain on average more than one reactive group to crosslink.

The monomers are preferably covalently reactive, and thus form a covalently crosslinked gel. The crosslinked gels are elastic, and further are both elastic and compliant with soft tissue at low polymer concentrations.

Any method of covalent polymerization is potentially useful in the formation of the gels. The reactive groups may include, without limitation, ethylenically unsaturated groups, isocyanates, hydroxyls and other urethane-forming groups, epoxides or oxiranes, sulfhydryls, succinimides, maleimides, amines, thiols, carboxylic acids and activated carboxyl groups, sulfonic acids and phosphate groups. Ethylenically unsaturated groups include acrylates and other unsaturated carboxylic acids, vinylic and allylic groups, cinnamates, and styrenes. Activated carboxyl groups include anhydrides, carbonylimidazoles, succinimides, carbonyl nitrophenols, thioesters, O-acyl ureas, and other conjugated carbonyls. In general, any reactive group that will covalently bond to a second and that can maintain fluidity when exposed to water for enough time to allow deposition and reaction is of use in making a suitable reactive macromer. Due to their excellent stability and slow reactivity in aqueous solutions, ethylenically unsaturated reactive groups are preferred.

The polymerization reaction does not have to result in covalent bonds. A number of materials are known which can form gel structures by changing the ionic conditions of the medium (e.g. alginate) or by changing the temperature of the medium (e.g., agarose, certain poloxamers). Polysaccharides are typical of these materials. Gel-like structures can be formed from proteins, such as gelatin or fibrin. While it maybe more difficult to get these materials to adhere strongly to tissue, they are potentially of use in the hydrogels, particularly as depots for the drug.

Gel formation can be accelerated by inclusion of small (non-macromeric) polymerizable molecules that can assist in linking larger, polymeric macromers. These typically have molecular weights less than about 100 Da, more preferably less than 500 Da. For free radical polymerization, any of the common ethylenically unsaturated molecules can be used. These include derivatives of acrylic and methacrylic acid, such as acrylamide, hydroxyethyl methacrylate (HEMA), and diacrylated or polyacrylated glycols and oligoglycols. Allyl groups (e.g., allyl glycidyl ether) and vinyl groups (e.g., N-vinyl caprolactam and N-vinyl pyrrolidone) are also of use. Other unsaturated compounds include cinnamic acid and its esters, and maleic, fumaric and itaconic acids and their derivatives.

Polymerization is initiated by any convenient reaction, including photopolymerization, chemical or thermal free-radical polymerization, redox reactions, cationic polymerization, and chemical reaction of active groups (such as isocyanates, for example.) Polymerization is preferably initiated using photoinitiators. Photoinitiators that generate a free radical or a cation on exposure to UV light are well known to those of skill in the art. Free-radicals can also be formed in a relatively mild manner from photon absorption of certain dyes and chemical compounds. The polymerizable groups are preferably polymerizable by free radical polymerization. The preferred polymerizable groups are acrylates, diacrylates, oligoacrylates, methacrylates, dimethacrylates, oligomethacrylates, cinnamates, dicinnamates, oligocinnamates, and other biologically acceptable photopolymerizable groups.

These groups can be polymerized using photoinitiators that generate free radicals upon exposure to light, including UV (ultraviolet) and IR (infrared) light, preferably long-wavelength ultraviolet light (LWUV) or visible light. LWUV and visible light are preferred because they cause less damage to tissue and other biological materials than short-wave UV light. Useful photoinitiators are those which can be used to initiate polymerization of the macromers without cytotoxicity and within a short time frame, minutes at most and most preferably seconds. Exposure of dyes, preferably in combination with co-catalysts such as amine, to light, preferably visible or LWUV light, can generate free radicals. Light absorption by the dye causes the dye to assume a triplet state, and the triplet state subsequently reacts with the amine to form a free radical which initiates polymerization, either directly or via a suitable electron transfer reagent or co-catalyst, such as an amine. Polymerization can be initiated by irradiation with light at a wavelength of between about 200-1200 nm, most preferably in the long wavelength ultraviolet range or visible range, 320 nm or higher, and most preferably between about 365 and 550 nm. Numerous dyes can be used for photopolymerization. Suitable dyes are well known to those of skill in the art. Alternatively, suitable chemical, thermal and redox systems may initiate the polymerization of unsaturated groups by generation of free radicals in the initiator molecules, followed by transfer of these free radicals to the unsaturated groups to initiate a chain reaction. Examples include but are not limited to peroxides, other peroxygen compounds, and azobisbutyronitrile.

As used herein, a "biodegradable" material is one that decomposes under normal in vivo physiological conditions into components that can be metabolized or excreted. Functional groups having degradable or resorbable linkages are incorporated into the structure of the hydrogel matrix to provide for its resorption over time. These functional groups may be incorporated within the macromers to form part of the backbone of the polymer strands of the hydrogel or as crosslinks between the polymer strands. Examples of degradable units may include, but are not limited to, esters, carbonates, carbamates and the like. The length of time it takes for the hydrogel to biodegrade may be tailored to provide a hydrogel that persists long enough to generate the required tissue level of the drug through the treatment period, which can last up to the seventh postoperative day, or preferably up to the tenth or fourteenth day. Given the achievement of this objective, shorter degradation or resorption times such as less than about three months are generally preferred. Degradation or resorption times less than about fifteen days are particularly preferred.

As used herein, a "biocompatible" material is one that stimulates only a mild, often transient, implantation response, as opposed to a severe or escalating response. Biocompatibility may be determined by histological examination of the implant site at various times after implantation. One sign of poor biocompatibility can be a severe, chronic, unresolved phagocytic response at the site. Another sign of poor biocompatibility can be necrosis or regression of tissue at the site. In the preferred embodiment, a biocompatible material elicits a minimal or no fibrosis or inflammation. This can be achieved through selection of hydrogel composition, and particularly through the use of hydrogel components resulting in degradation of the hydrogel in vivo in less than about two weeks, more preferably within seven to ten days.

In a preferred embodiment, the hydrogel composition is selected to provide acceptable levels of fibrosis or tissue reaction. This can be achieved through the selection of the reactive formulation, and other techniques known to those skilled in the art in drug delivery utilizing polymeric delivery devices.

Preferably, the inotropic agents are poorly soluble in water (i.e. hydrophobic). In terms of the solubility classification of the United States Pharmacopoeia (USP 24/NF 19, effective Jan. 1, 2000; p. 2254), the preferred solubility classes are: "slightly soluble", requiring 100 to 1000 parts of solvent to dissolve; "very slightly soluble", requiring 1000 to 10,000 parts of solvent; and "practically insoluble, or insoluble", requiring over 10,000 parts of solvent. Collectively, these classes are defined herein as "poorly soluble".

An inotropic agent applied in a single application directly to the heart is expected to be similarly or more effective to intravenous administration, with a potential reduction in side effects because a lower required dose and limited spread is anticipated.

The slow dissolution rate for poorly soluble inotropic agents controls their rate of efflux from the gel. The rate of efflux for such inotropic agents can also be controlled by selecting the particle size of the drug particles that are suspended in the macromer solution before its polymerization. Particles of a particular size can be made by any known method, including grinding, milling, cryofracture, precipitation, spraying, spray drying, and/or classification. Dispersion and stabilization of the particles within the macromer solution may be achieved with the use of surfactants.

When more soluble inotropic agents are used, their efflux rate from the gel can be altered to achieve the necessary delivery rate. Such soluble inotropic agents include those falling in United States Pharmacopoeia classes "very soluble", "freely soluble", "soluble", and "sparingly soluble". Typical means of altering release rates include encapsulating the agents in micro particles or liposomes and conjugating the agents to macromolecules. They can be made less soluble by altering the salt or using the free acid/base form of the agents.

In one embodiment, pre-encapsulation is used for the small, water-soluble drugs (typically of molecular weights less than 1000 Da) that are incorporated into hydrogels, to decrease the rate of release of these drugs. The encapsulation may be by any conventional means. One means is entrapment in micro particles of a degradable, water-insoluble polymer. Typical materials are polymers and copolymers of lactic acid, glycolic acid, and copolymers thereof (e.g., PLGA). Other materials used to form suitable micro particles are copolymers of ethylene and vinyl acetate (EVAC) and polymers of anhydrides, such as poly sebacic anhydride. Particles of drug may also be pre-encapsulated with polymers such as EVAC and PLGA, or with thin layers of materials that dissolve in vivo, for example, the enteric coatings or other coatings typically used for oral delivery, such as gelatin.

Release of more soluble inotropic agents can be slowed by conjugating small molecules to polymers by degradable or reversible linkages. Many such systems are described in the art. In one embodiment, such systems are generated by immobilizing a binding or targeting molecule for the drug, such as an antibody or lectin, which is saturated with the drug, in the gel. In another typical embodiment, drug is attached to a polymer bearing reactive groups, such as to the hydroxyl of polyvinyl alcohol, to a carboxyl, sulfonate or amine group of a polysaccharide or the hydroxyl or carboxyl of an alpha-hydroxy acid (e.g., lactic or glycolic acid), or to a carboxylic group on a polymer (e.g., alginate, polyacrylic acid) via an anhydride, an ester, a carbonate, or carbamate linkage. Many similar methods are described in the art.

The solubility of some agents can be decreased by preparing them in their neutral ("free base") form. Such agents often can also be administered as suspensions in oil, which in turn is dispersed in water, usually with surfactant stabilizers.

The level of loading of the inotropic agent in the delivery vehicle will normally be as high as practical, while leaving a margin of loading to prevent premature precipitation or aggregation, or inhibition of gel formation. The concentration of the inotropic agent can be between 0.5 and 1% by weight, but this will depend in part upon the source and form of the inotropic agent. Gel polymerization rate and final gel may be significantly affected by drug concentration. Use of other macromers affects the optimal level. Fortunately, acceptable loading ranges are easily determined for a particular system by varying the loading and determining the properties of the formed gel.

In one method, the inotropic agent is provided in a formulation that forms a hydrogel in vivo, i.e. after its components are administered to the heart.

In a second method, the inotropic agent is provided to the patient in a preformed hydrogel "patch", i.e. formed before administration to the heart.

The hydrogels of the present invention are formed by a polymerization reaction, which may be any reaction that can be carried out in a substantially aqueous environment and is not damaging to tissue. The gels may be polymerized in vivo or in vitro.

The adherence of gels to tissue can be optimized by techniques that employ functional primers, as described in U.S. Pat. No. 5,800,373 to Melanson et al., U.S. Pat. No. 5,844,016, or 5,900,245 to Sawhney et al. for gels formed by polymerization of ethylenically unsaturated precursors. Suitable gel compositions form strong bonds to tissue. These techniques are also applicable to creating strong adherence of the materials to tissue, including tissue to which it is difficult to obtain adherence by conventional methods, for example, cartilage.

A general procedure for applying materials to the tissue involves brushing or dabbing primer over a larger area than that over which the material is applied. Thereafter, material is brushed or dabbed over the deposited primer. Then bulk material is applied by dripping (if liquid) or spreading (if paste) over yet a smaller area of the treated zone. Then light (at appropriate wavelength, intensity, distance and for an appropriate time) is applied at each zone, or other means of polymerizing the material are used.

Methods for in vivo and in vitro hydrogel polymerization are known in the art, for example as described in published patent applications 20020150622 and 20050004428, which are hereby incorporated by reference.

For in vivo polymerization, the inotropic agent is formulated in appropriate excipients (if any) in a vial, and is taken up in a known amount of hydrogel forming material. This solution is applied to the tissue, and polymerization is effected to form a gel adherent to the tissue. Preferably, the solution is polymerized by illumination of a photoinitiator or photosensitizer in the solution. In this case, the mixing of two solutions at the time of application will not necessarily form a gel; however once the solutions are illuminated by light of an appropriate frequency, a gel will form, as described in U.S. Pat. No. 5,410,016 to Hubbell et al. incorporated herein by reference in its entirety.

In vivo polymerization has the advantage of being able to produce "good" to "excellent" adherence when polymerized on the tissue surface. This is particularly true when the tissue is first primed or otherwise pretreated with an agent (primer) stimulating polymerization (as known to those skilled in the art, for example, as described in U.S. Pat. No. 5,844,016 to Sawhney et al. and U.S. Pat. No. 5,834,274 to Hubbell et al. incorporated herein by reference in their entirety) prior to the application of the macromer composition containing the inotropic drug. See also U.S. Pat. Nos. 5,567,435; 5,844,016; 5,986,043; 6,060,582; and 6,306,922 incorporated herein by reference in their entirety. In these methods, an aqueous solution containing a photoinitiation system, including one or more photoinitiators, photosensitizers and co-initiators, amine or amide electron transfer agent, redox accelerant system for the photoinitiation system (such as a metal ion and a peroxide); and a photopolymerizable macromer solution, are applied to the tissue, and the solution is polymerized by exposure to UV or visible light at room or body temperature.

For in vitro polymerization, hydrogel patches containing the inotropic agent are polymerized in vitro and then adhered to the surface of the heart. The inotropic agent in any suitable formulation can be entrapped in a hydrogel in vitro, which is optionally preserved by freezing or drying, and is subsequently transferred to the cardiac tissue. The preformed gel patch, or more than one preformed gel patch, is then adhered to the cardiac tissue. Adhesion of the patch may be achieved by the polymerization of a hydrogel-forming material, which may be the same as or different from the material used to form the gel patch, placed between the preformed gel patch and the tissue, or optionally encapsulates the entire pre-formed gel. Adhesion may also be achieved by completing polymerization of a partially polymerized gel patch onto the tissue. A partially polymerized gel patch is prepared by reducing time exposure to polymerization conditions or by quenching polymerization.

In vitro polymerization has the advantage of providing a reliable means of delivering a precisely defined dose of the inotropic agent. The preformed gels should have the same properties as gels formed in vivo. This method of application may be regarded as another form of application of an encapsulated drug to the tissue, since the adhesion to the tissue is provided by a hydrogel that is formed in situ on the tissue. The preferred method of attaching the gels to the tissue surface is to use macromer solutions to adhere the preformed gel to the tissue. Adherence is also preferably in the "good" to "excellent" range.

A material is tissue adherent if it requires a force to remove the material from the tissue. Thus, the general and practically useful measurement of adherence is that the gel, when applied to the tissue, remains attached to the tissue for at least as long as is required to obtain the therapeutic effect of the drug. Typically, this time period will be sufficiently long to observe at least about 10% elution of the drug, and preferably 20% elution or more, before detachment or degradation of the gel.

Ex vivo tests can be used to determine a material's potential adherence. In evaluating potential adherence of materials, it is useful to have an in vitro test to determine formulations that are likely to have the desired degree of adherence to the tissue surface. One method of judging adherence is to require that upon a gradual increase in a detaching force, the force required to remove the gel from the tissue is greater than or approximately equal to the force required to cause cohesive failure of the gel (or the tissue, if lesser). Thus on attempting to remove the material, either the material or the tissue experiences cohesive failure at a lesser force than, or at approximately the same force as, the force at which the bond between the material and the tissue experiences adhesive failure. Materials that require a force of about 20 dynes/cm$^2$ to remove them from the tissue are sufficiently adhesive for delivery of inotropic agents.

Adherence can be described qualitatively as "excellent", when cohesive failure is required for removal from the surface, "good" when failure is partially cohesive and partially adhesive, "fair" when removal requires only adhesive failure. (i.e., detachment of the gel from the surface) and more than 20 dynes/cm$^2$ of force is required to produce adhesive failure, and "poor" if none of these criteria are satisfied. Force can be measured using a mechanical properties tester, such as an Instron™ tester or other device.

The delivery vehicles of the invention are preferably highly compliant with the tissue to which they adhere. Thus, the delivery vehicles stretch and bend along with the tissue. Cardiac tissue is in continual motion, and the delivery vehicle should not significantly disturb this motion. It is preferable that the response to stress within these limits be substantially elastic, i.e., reversible. Thus the delivery vehicle should remain as a coherent material for at least the period required for delivery of the inotropic agent.

Techniques for producing strong adherence of a preformed hydrogel, a patch, or other delivery vehicle to the cardiac tissue include applying an initiator or promoter of polymerization to the tissue at the site; applying a thin layer of gelling solution having a high concentration of a polymerizable reagent at the site; applying materials bearing one half of a reactive pair to the site, optionally a member of a reactive pair which is also reactive with tissue; and applying mechanical action to a layer of polymerizable material on the tissue (before polymerization) to ensure that no layer of fluid, such as mucus or the like, separates the polymerizable material from the tissue.

As described herein, the delivery vehicles of the invention, including hydrogels, patches, ointments and creams, can be applied at the time of surgery and the drug delivered directly to the affected cardiac tissue. For a hydrogel polymerized in situ, the gel can be applied in open surgery by any method. In one embodiment, the delivery vehicle such as an ointment, cream, or gel is preferably brushed or sprayed onto the tissue surface for example by using a device designed for percutaneous use, but may be dripped from a mixing apparatus.

The therapeutic compositions of this invention are administered by local administration to the heart, as by application of a patch, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

It is important to provide a way for the physician to deliver a well-defined amount of the inotropic agent, so that the therapeutic effect can be obtained.

The dosage of the inotropic agents for use in a human or animal and the minimum duration can be determined with only routine experimentation in view of animal studies and the known drug kinetics, including half-life, solubility and other readily ascertainable properties. The effective dosage can be determined from tissue concentrations and physiological effects over time in cardiac tissue of animals, after application of a known concentration of the drug in the delivery vehicle. Such animal studies are routine in determining dosage for any drug. The dosage of the inotropic agent will also be optimized based on the period of time over which delivery is to be obtained and the release rate from the delivery vehicle, as well as the degradation characteristics of the delivery vehicle, to deliver a therapeutically effective dose to the heart tissue.

The compositions are administered in a manner compatible with the dosage formulation, and in a therapeutically effective amount. The quantity to be administered and timing depends on the subject to be treated, capacity of the subject's myocardium to utilize the active ingredient, and degree of therapeutic effect desired. Precise amounts of active ingredient required to be administered depend on the judgment of the practitioner and are peculiar to each individual.

Any formulation containing the active ingredients, which is suitable for the intended use, as are generally known to those of skill in the art, can be used. Suitable pharmaceutically acceptable carriers are known to those of skill in the art. The carrier must be pharmaceutically acceptable in the sense of being compatible with the other ingredients of the formulation and not deleterious to the recipient thereof.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects.

In one embodiment, the inotropic agent may be administered in liposomes or microspheres or microparticles. Methods for preparing liposomes and microspheres for administration to a patient are well known to those of skill in the art. U.S. Pat. No. 4,789,734, the contents of which are hereby incorporated by reference, describes methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is provided by G. Gregoriadis, Chapter 14, "Liposomes," Drug Carriers in Biology and Medicine, pp. 287-341 (Academic Press, 1979).

Microspheres formed of polymers or proteins are well known to those skilled in the art, and can be tailored for direct administration to the heart using the delivery vehicles of the present invention. Suitable liposomes for targeting ischemic tissue are generally less than about 200 nanometers and are also typically unilamellar vesicles, as disclosed, for example, in U.S. Pat. No. 5,593,688 to Baldeschweiler, entitled "Liposomal targeting of ischemic tissue," the contents of which are hereby incorporated by reference.

Preferred microparticles are those prepared from biodegradable polymers, such as polyglycolide, polylactide and copolymers thereof. Those of skill in the art can readily determine an appropriate carrier system depending on various factors, including the desired rate of drug release and the desired dosage.

The formulations may further include one or more optional accessory ingredient(s) utilized in the art of pharmaceutical formulations, e.g., diluents, buffers, binders, surface active agents, thickeners, lubricants, suspending agents, preservatives (including antioxidants) and the like. The preparation of a pharmacological composition that contains active ingredients dissolved or dispersed therein is well understood in the art and need not be limited based on formulation.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The compositions of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

As with the use of other pharmaceutical compositions, the individual patient can be monitored by various ways, including but not limited to invasive hemodynamic monitors, including arterial and central venous pressure monitoring; pulmonary artery catheters, which can include hemodilution cardiac output monitors, and/or continuous mixed venous oxygen saturation monitoring, in addition to pulmonary artery and pulmonary capillary wedge pressures; transesophageal or transthoracic echocardiography; and continuous electrocardiographic monitoring.

EXAMPLES

Methods

Sprague Dawley rats (900 g-1100 g) were anesthetized with an intraperitoneal injection of ketamine and xylazine. The rat was laid on a heating pad and maintained euthermic with warming lights. A 24 gauge intravenous catheter was placed in the tail vein and Ringer's lactate solution (LR) was infused at 10 cc/hr. The trachea was exposed through a vertical incision and cannulated with a 16 gauge blunt cannula that served as an endotracheal tube. The tube was connected to a ventilator for control of ventilation and respiration. The respiratory rate was set to 60 breaths per minute, inspiratory to expiratory time was set to 1:2 and inspiratory flow was 2 liters per minute. A midline sternotomy was performed, the heart exposed and the pericardium resected. The right carotid artery was dissected clean of fascia and care was taken to preserve the adjacent vagus nerve. A polyethelene (PE-50) cannula was inserted via an arteriotomy into the carotid artery and advanced through the ascending aorta into the left ventricle. This ventricular cannula was connected to a high fidelity pressure transducer and digital data acquisition system to record hemodynamic measures. Heart rate (HR), left ventricular systolic blood pressure (SBP), and the maximum rate of change of blood pressure in the left ventricle during isovolemic contraction (dp/dt max) was all recorded. The dp/dt max is the gold standard index of myocardial contractility.

Following cannulation the rat was stabilized for 30 minutes. Five-second recordings of HR, SBP and dp/dt max were captured every 3 to 5 minutes. SBP and dp/dt max were averaged over all the beats captured in the 5-second interval. Dobutamine (313 mcg/ml), a potent beta agonist inotropic agent, was delivered to the left ventricular free wall through the sternotomy using an infusion pump connected to a 24 gauge IV cannula that was suspended directly over the heart (4 mcg/min, 0.8 ml/hr). In this fashion, drug was administered directly to the heart and only in the area exposed by resected pericardium. After 30 minutes the pericardial application of dobutamine was terminated and hemodynamic measurements were recorded for an additional 30 minutes.

Results

Figure 2:
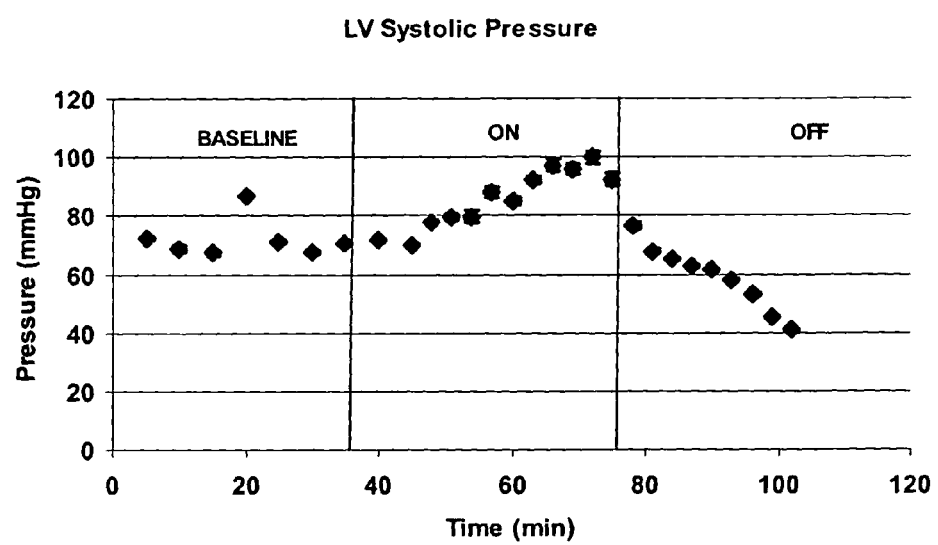
FIG. 2 shows left ventricular systolic blood pressure over time in rats administered Dobutamine, a nonselective beta agonist inotropic agent, which was delivered directly to the left ventricular wall. Local pericardial delivery of dobutamine increased systemic blood pressure. It is known that intravenous infusion of inotropic agents reduce systemic blood pressure.
Figure 3:
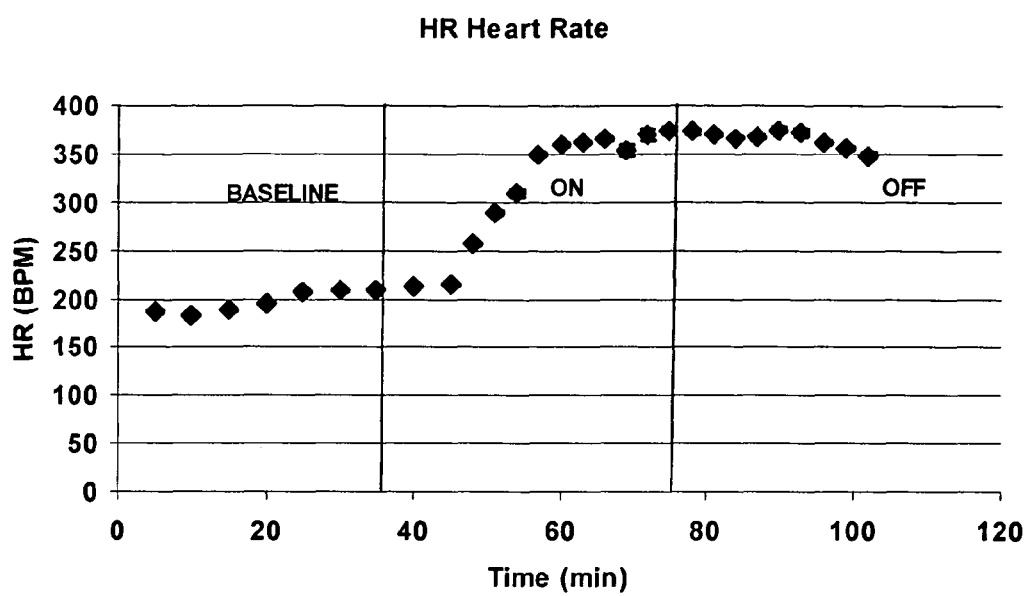
FIG. 3 shows heart rate over time in rats administered Dobutamine, a non selective beta agonist inotropic agent, which was delivered directly to the left ventricular wall.

The HR, SBP and contractile response (dp/dt max) to the pericardial application of dobutamine are shown in FIGS. 1-3.

This experiment demonstrates that dobutamine can be applied directly to the myocardial surface and exert positive inotropic effects without the systemic effects seen with systemic infusion. Contractility, as expressed by the maximum dp/dt of the left ventricular pressure during isovolemic contraction increased significantly and shortly after dobutamine was applied to the free surface of the heart (FIG. 1). Dobutamine given in an intravenous infusion, in addition to increasing myocardial contractility and cardiac output, dilates smooth muscle through peripheral beta-receptors and leads to vasodilatation and reduction in systemic blood pressure. In this experiment, local pericardial dobutamine-increased systemic blood pressure, likely from increased force of contraction and cardiac output in the presence of constant vascular tone (FIG. 2). This suggests that the usual peripheral vasodilatory side effects of dobutamine infusion were eliminated by local application to the heart. Dobutamine is also a potent chronotrope and topical application with possible diffusion to the sino-atrial node, which normally functions as the pacemaker for the heart, increased heart rate (FIG. 3). These data show that potent inotropic agents such as sympathomimetics and phosphodiesterase inhibitors can be locally applied to the heart and improve contractile function, while minimizing systemic side effects.

All references described herein are incorporated by reference in their entirety.

We claim:

1. A method of delivering a positive cardiac inotropic agent to the heart of a human subject, comprising:
providing a delivery vehicle which is in the form of an adherent patch which comprises at least one positive inotropic agent and a barrier that is non-permeable to the positive inotropic agent, the barrier being effective to allow release of the positive inotropic agent toward the myocardium and to minimize release into the pericardial fluid;
adhering the delivery vehicle onto an outer surface of the heart away from the sinoatrial node of a subject in need of treatment; and
releasing a therapeutically effective amount of the positive inotropic agent in a controlled manner from the delivery vehicle directly to the heart to increase the force of myocardial contraction.

2. The method of claim 1, wherein the adherent patch is biodegradable.

3. The method of claim 1, wherein the positive inotropic agent is a sympathomimetic compound.

4. The method of claim 1, wherein the inotropic agent is a phosphodiesterase inhibitor.

5. The method of claim 1, wherein the delivery vehicle is placed on the left ventricular wall or apex of the ventricle and away from the sinoatrial node or the right atrium of the heart.

6. The method of claim 1, wherein the inotropic agent is an agent that interacts with the sympathetic nervous system and modulates calcium entry, G-proteins, ATP, or GTP, wherein the inotropic agent is selected from the group consisting of sympathomimetic compounds, phosphodiesterase inhibitors, BNP, ANP, and digitalis glycosides.

7. The method of claim 1, wherein the inotropic agent is a sympathomimetic compound selected from the group consisting of epinephrine, norepinephrine, dobutamine, isoproterenol, salbutamol, salmeterol, terbutaline, phenylephrine, ephedrine, clonidine and dopamine.

8. The method of claim 1, wherein the inotropic agent is a phosphodiesterase inhibitor selected from the group consisting of milrinone, enoximone and amrinone, and derivatives and analogues thereof.

9. The method of claim 1, wherein the subject is a surgical patient and is selected from the group consisting of a cardiac surgery patient, a thoracic surgery patient, and a general surgery patient.

10. The method of claim 1, wherein the subject is a cardiac surgery patient, and wherein the cardiac surgery patient is selected from the group consisting of a cardiac surgical patient requiring support from a cardiopulmonary bypass circuit and a cardiac patient not requiring support from a cardiopulmonary bypass circuit.

11. The method of claim 1, wherein the subject has a condition selected from the group consisting of trauma, shock, acute congestive heart failure, and chronic congestive heart failure.

12. The method of claim 1, wherein the delivery vehicle comprises a polymeric material in which said positive inotropic agent is mixed.

13. The method of claim 1, wherein the delivery vehicle is placed directly onto the heart via an open surgical wound.

14. The method of claim 1, wherein the inotropic agent is administered to said subject during a time period selected from the group consisting of prior to a CPB surgery, during a CPB surgery, subsequent to a CPB surgery, and combinations thereof.

15. The method of claim 1, wherein placement of the delivery vehicle onto the heart comprises passing the delivery vehicle through a catheter or port.

16. The method of claim 1, wherein the delivery vehicle is sufficiently compliant to not impede cardiac contraction.

* * * * *